United States Patent
Di Lauro

(10) Patent No.: US 10,206,718 B1
(45) Date of Patent: Feb. 19, 2019

(54) IMPLANTABLE CONNECTOR

(71) Applicant: SeaSpine Orthopedics Corporation, Carlsbad, CA (US)

(72) Inventor: Michael Di Lauro, Carlsbad, CA (US)

(73) Assignee: SeaSpine Orthopedics Corporation, Carlsbad, CA (US)

( * ) Notice: Subject to any disclaimer, the term of this patent is extended or adjusted under 35 U.S.C. 154(b) by 0 days.

(21) Appl. No.: 15/436,308

(22) Filed: Feb. 17, 2017

Related U.S. Application Data

(60) Provisional application No. 62/296,260, filed on Feb. 17, 2016.

(51) Int. Cl.
| | |
|---|---|
| *A61B 17/88* | (2006.01) |
| *A61B 17/70* | (2006.01) |
| *A61B 17/86* | (2006.01) |
| *A61B 17/56* | (2006.01) |

(52) U.S. Cl.
CPC ...... *A61B 17/7052* (2013.01); *A61B 17/7004* (2013.01); *A61B 17/8665* (2013.01); *A61B 2017/564* (2013.01); *A61B 2017/867* (2013.01)

(58) Field of Classification Search
CPC ............ A61B 17/7052; A61B 17/7004; A61B 17/8665; A61B 2017/564; A61B 2017/867
USPC .................................................. 606/260, 278
See application file for complete search history.

(56) References Cited

U.S. PATENT DOCUMENTS

| | | | | |
|---|---|---|---|---|
| 5,334,203 A | * | 8/1994 | Wagner | A61B 17/7052 24/396 |
| 8,252,030 B2 | | 8/2012 | Iott et al. | |
| 8,337,532 B1 | * | 12/2012 | McLean | A61B 17/7011 606/250 |
| 8,628,559 B2 | | 1/2014 | Iott et al. | |
| 8,882,803 B2 | | 11/2014 | Iott et al. | |
| 9,364,264 B2 | | 6/2016 | Iott et al. | |
| 9,808,293 B2 | | 11/2017 | Iott et al. | |
| 9,814,493 B2 | | 11/2017 | Pham et al. | |
| 2002/0013585 A1 | * | 1/2002 | Gournay | A61B 17/7034 606/272 |
| 2007/0055242 A1 | * | 3/2007 | Bailly | A61B 17/7032 606/266 |
| 2008/0234743 A1 | * | 9/2008 | Marik | A61B 17/705 606/257 |
| 2010/0234893 A1 | * | 9/2010 | Iott | A61B 17/7035 606/278 |
| 2010/0268279 A1 | * | 10/2010 | Gabelberger | A61B 17/7035 606/278 |
| 2013/0018421 A1 | * | 1/2013 | George | A61B 17/7044 606/278 |
| 2016/0166289 A1 | * | 6/2016 | Alsup | A61B 17/7049 606/253 |

OTHER PUBLICATIONS

Spine Wave, Inc., Annex Adjacent Level System, 2015, 8 pages.
DePuy Spine, Inc., Expedium 5.5 Spine System, 2012, 15 pages.

* cited by examiner

*Primary Examiner* — Eduardo C Robert
*Assistant Examiner* — David C Comstock
(74) *Attorney, Agent, or Firm* — Middleton Reutlinger

(57) ABSTRACT

A rotational connector insertable into a surgical incision onto a top of a pedicle screw in a first orientation and rotated into a second orientation to engage a primary fusion rod. The rotational connector may include a revision rod coupled to one end thereof.

8 Claims, 18 Drawing Sheets

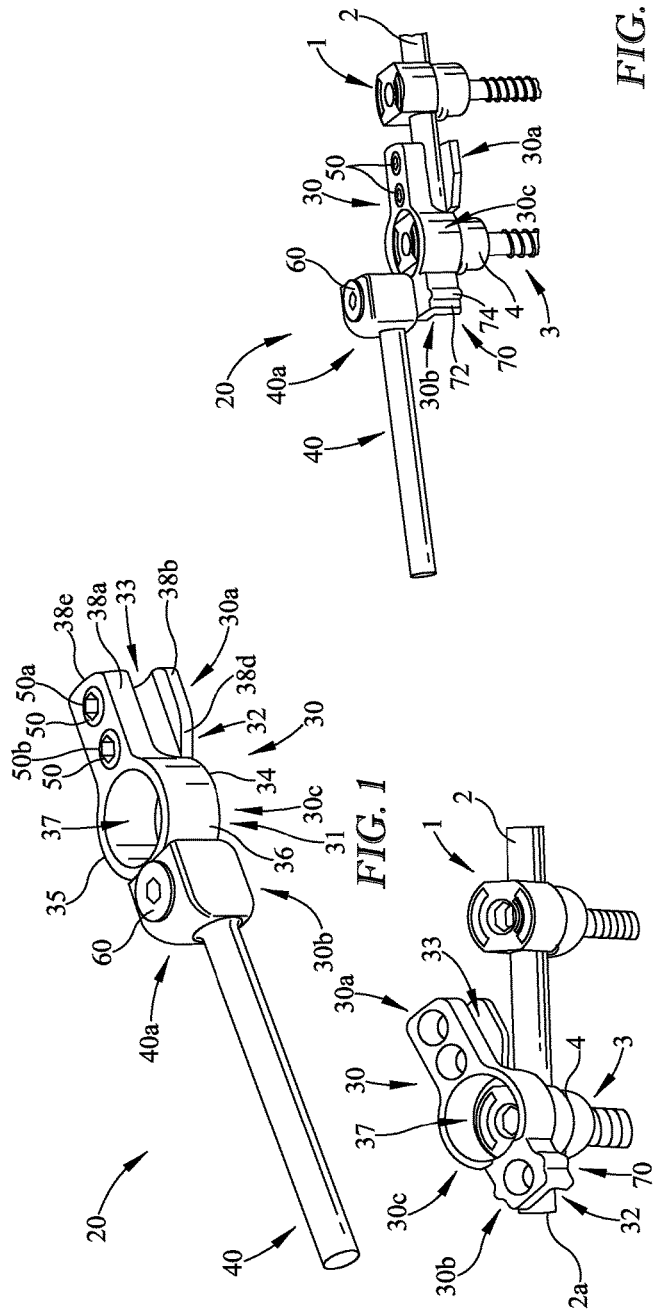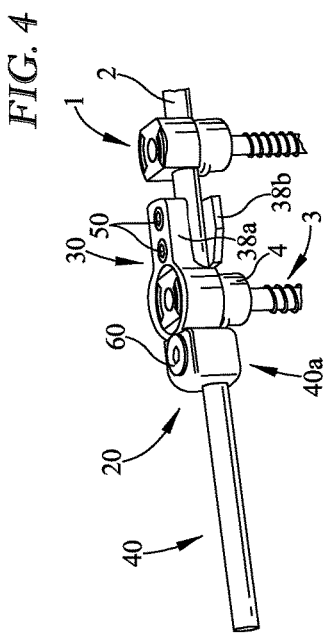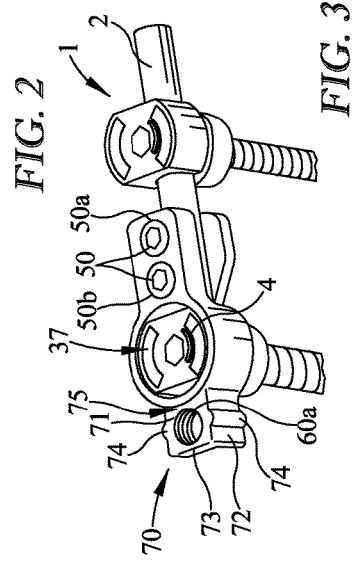
FIG. 1
FIG. 2
FIG. 3
FIG. 4
FIG. 5

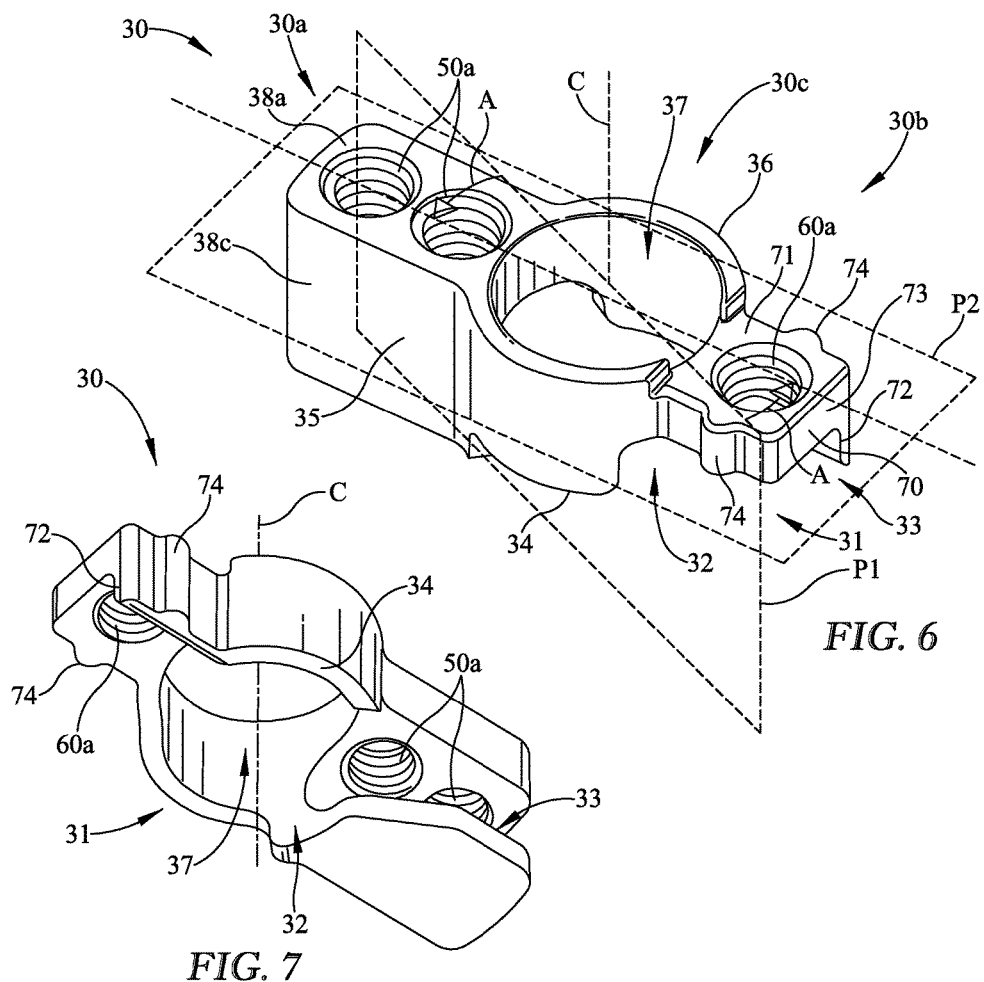
FIG. 6
FIG. 7
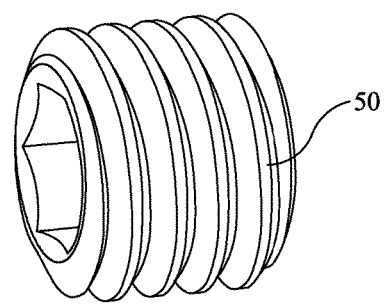
FIG. 8

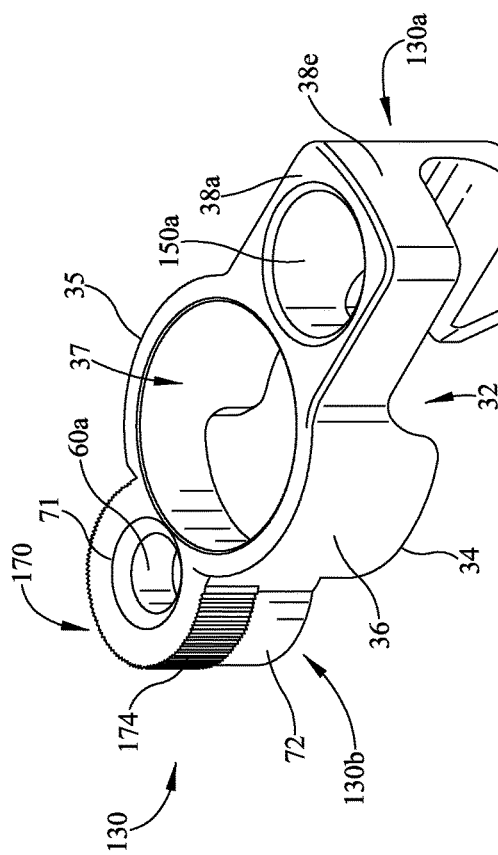
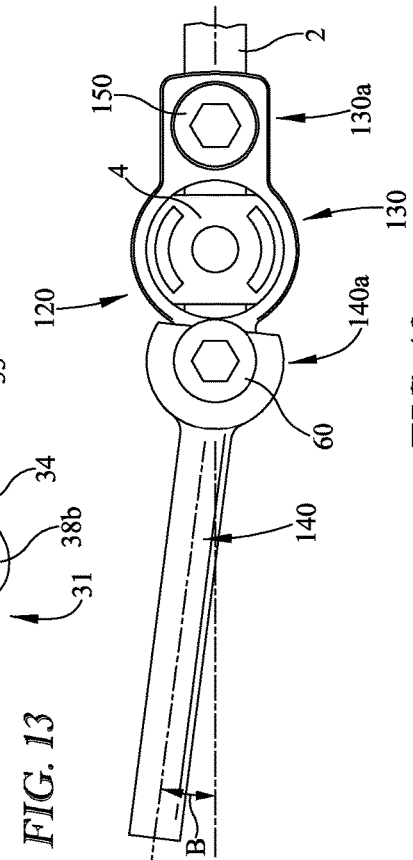
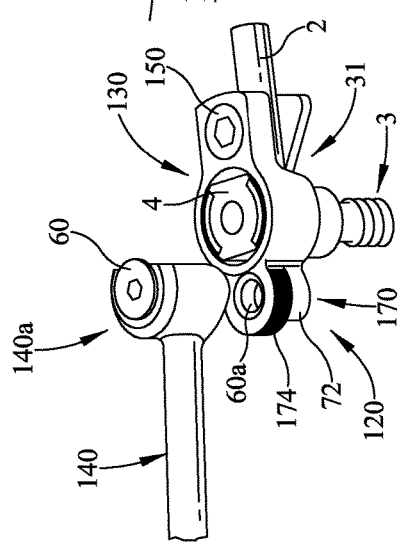

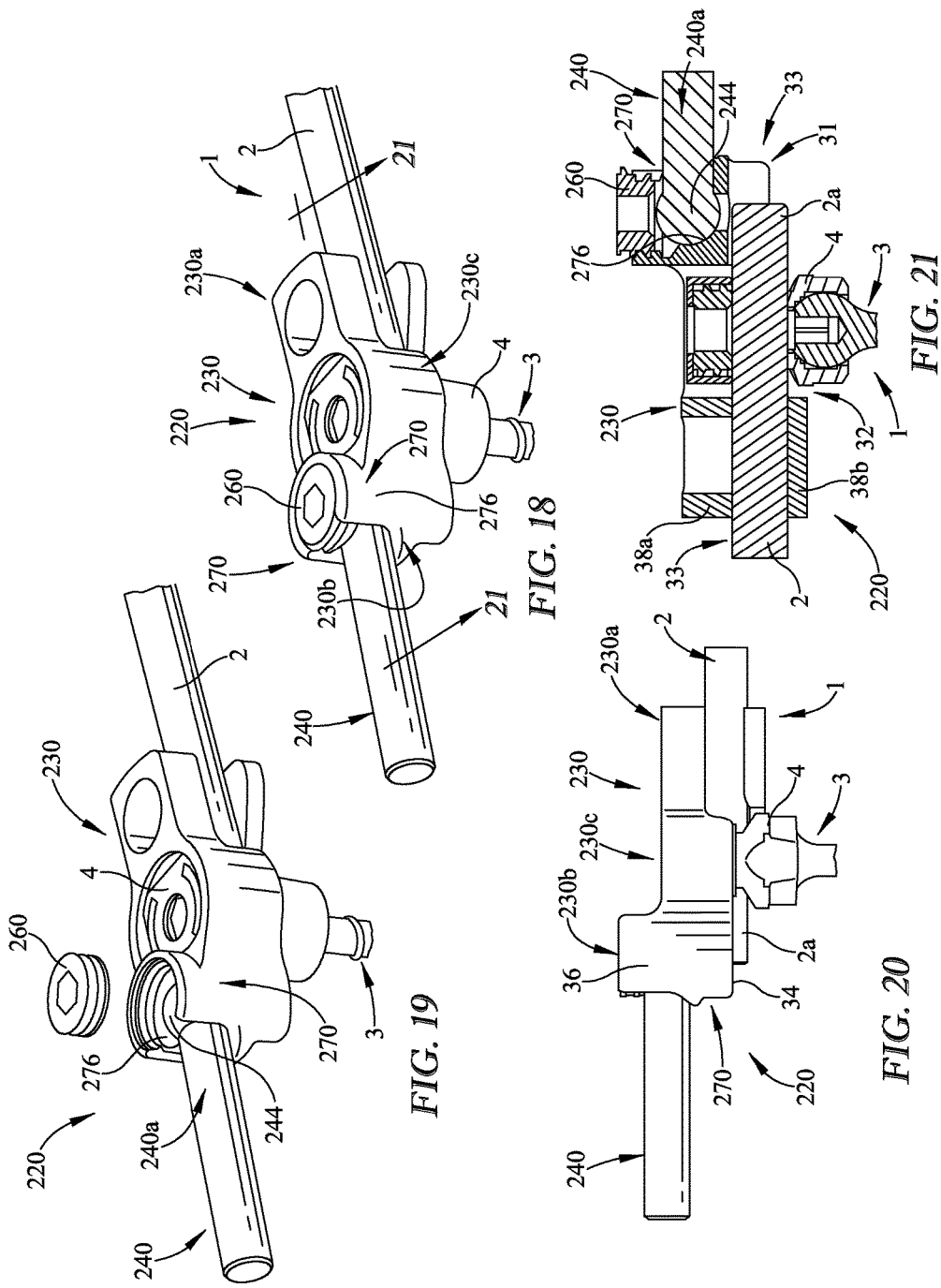

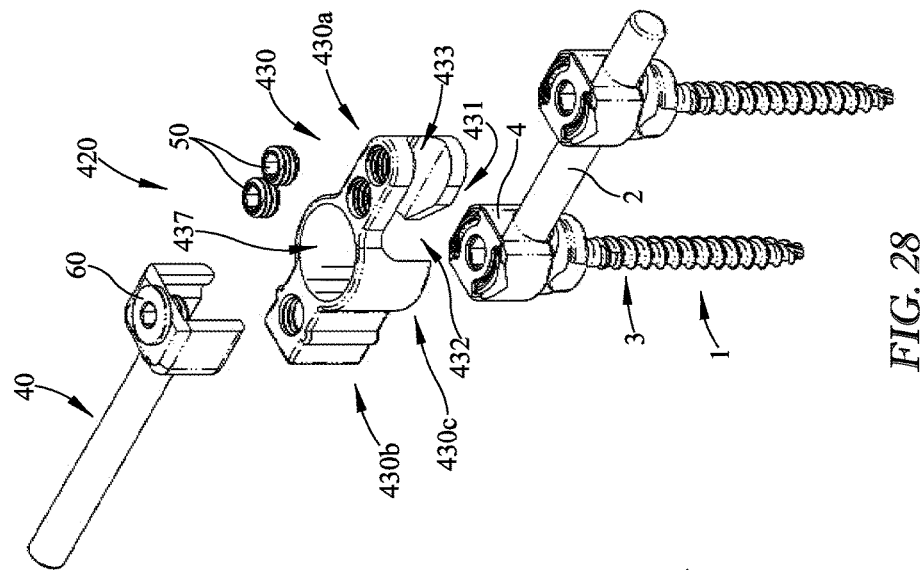
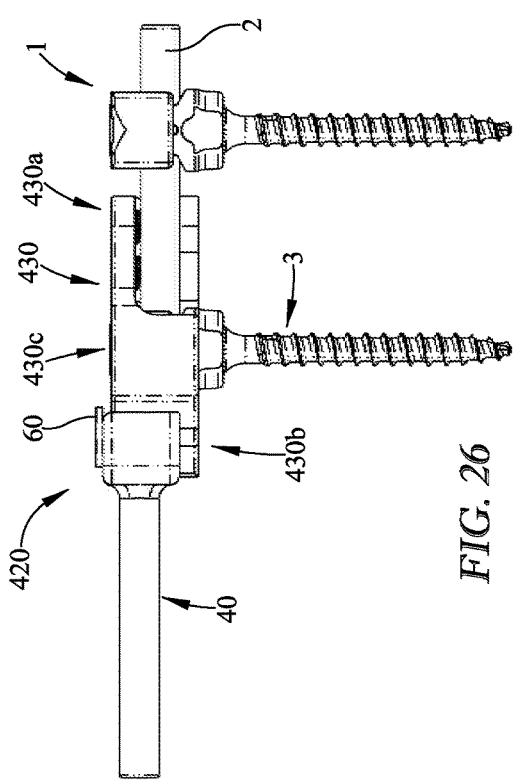
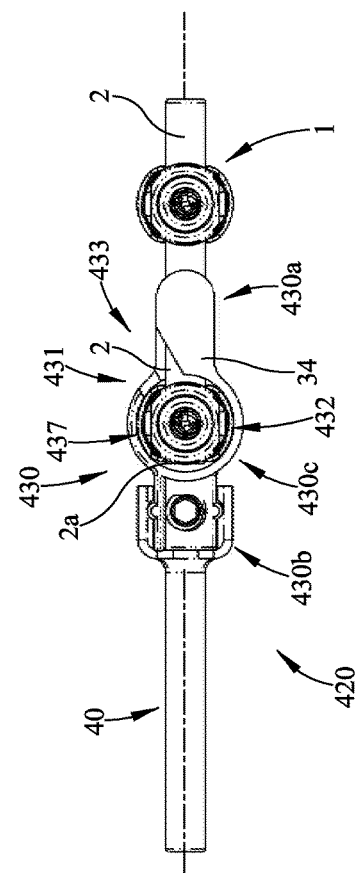
FIG. 28
FIG. 26
FIG. 27

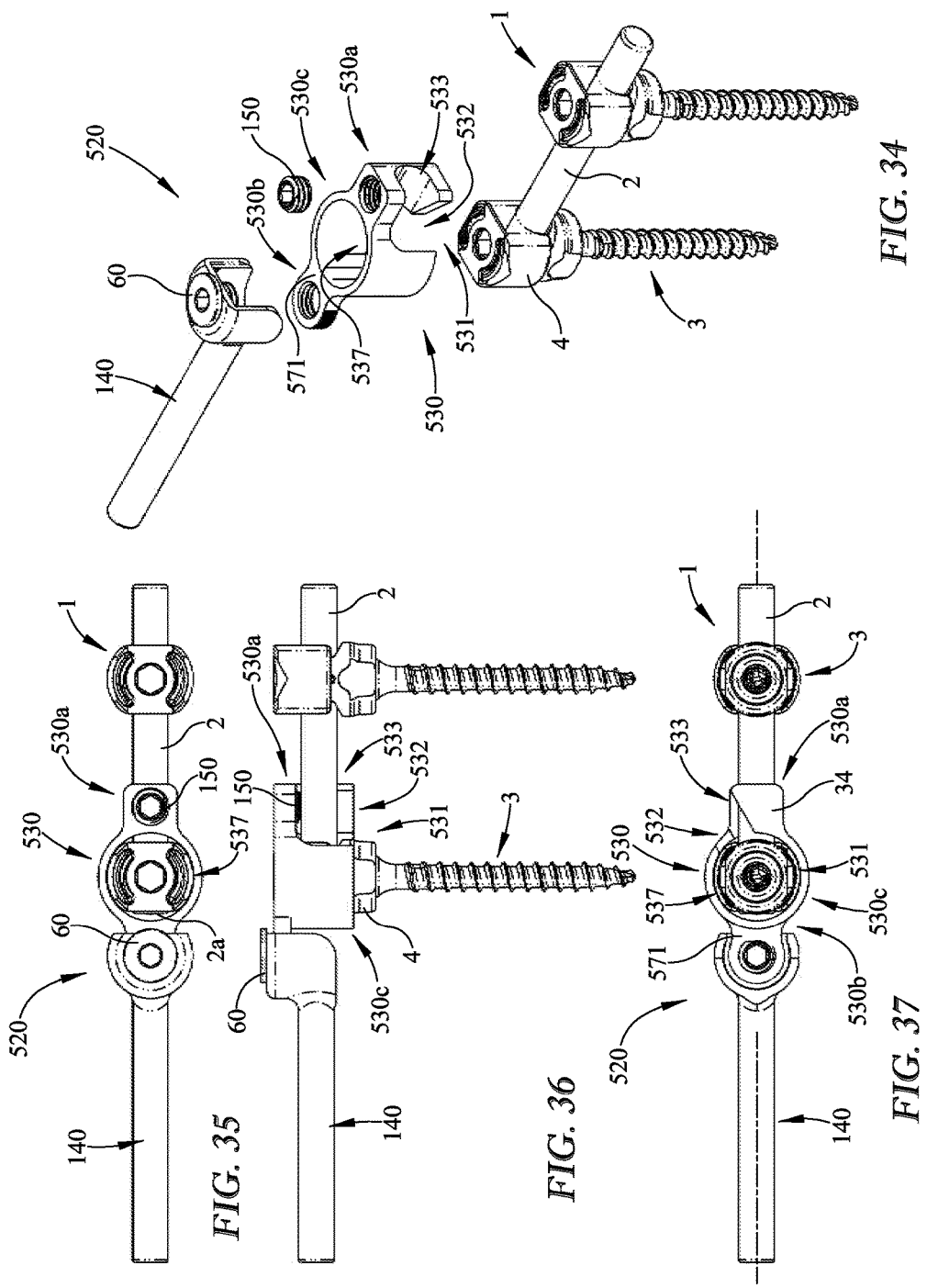

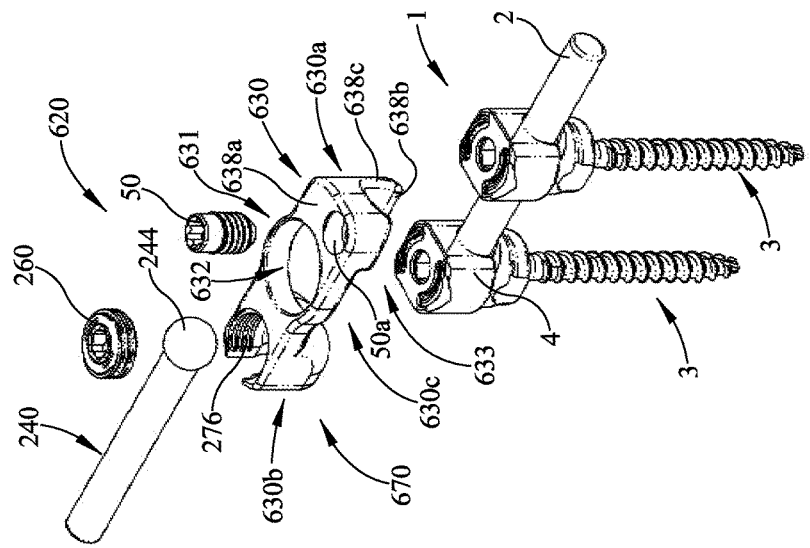
FIG. 39
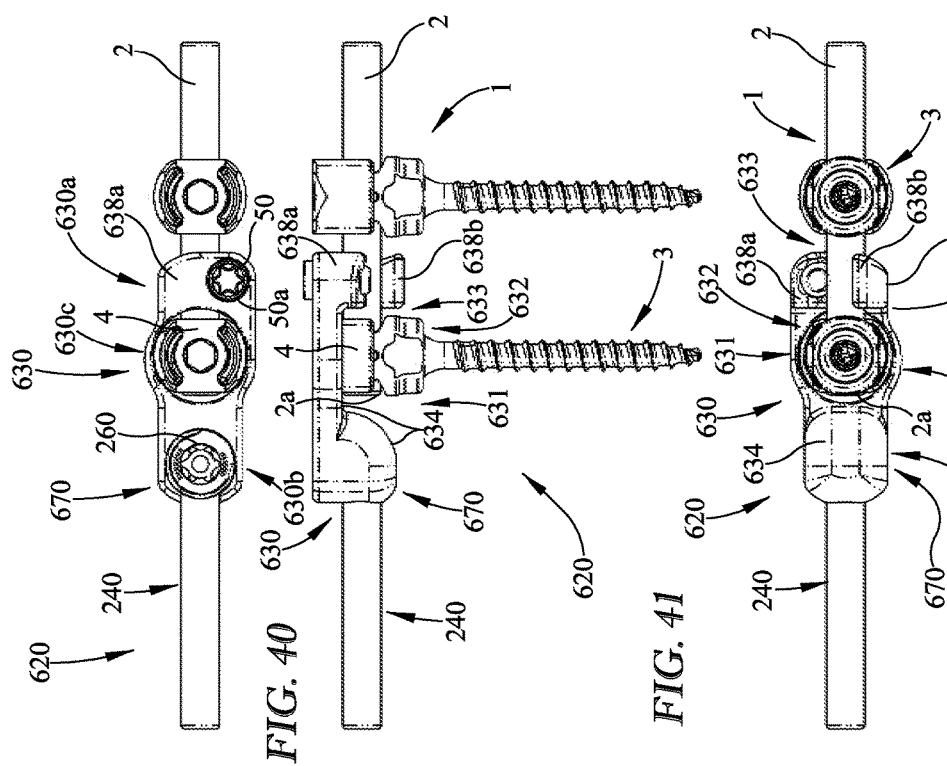
FIG. 40
FIG. 41
FIG. 42

IMPLANTABLE CONNECTOR

CROSS-REFERENCE TO RELATED APPLICATIONS

This application claims priority to and benefit from U.S. Provisional Application No. 62/296,260, filed Feb. 17, 2016, the entire contents of which is incorporated by reference in its entirety.

FIELD

The present disclosure is directed to methods and apparatus for implantable connection to a rod, such as a spinal rod.

BACKGROUND

Surgery, whether of the spine or other areas of the body, is often complex and routinely involves the need for highly experienced medical staff, in addition to well-designed and well-manufactured implants, made to exacting specifications. Often the implants take the form of various types of hardware. In the area of spinal fixation, for example, various spinal fixation devices have been developed in the art. Some examples of such fixation devices include spinal rods, plates, corpectomy cages, and intervertebral discs, to name but a few. Spinal fixation rods are fixation devices configured to fix adjacent vertebrae of a spine relative to each other. The rods provide stabilization of the spine till fusion occurs. The spinal fixation rods are often used in spinal surgeries to repair spinal abnormalities, whether related to injury or otherwise. The spinal rods are configured to attach to the vertebrae using, for example, anchoring devices like pedicle screws and hooks.

Patients often experience extreme and debilitating pain because of spinal column injuries or from spinal column disorders such as spondylolisthesis and scoliosis. Pain may be attributed to issues of the spine as related to degeneration, deformity, and/or injury. Often a typical course of treatment involves surgical spinal fixation utilizing spinal fixation rods that mechanically immobilize areas of the spine causing, ideally, the eventual fusion of the treated vertebrae.

Sometimes additional surgical procedures, known as revision surgeries, become necessary. Several causes exist for the need for revision surgeries. For example, pseudarthrosis (failure to achieve solid fusion) may have occurred, which can be due to various causes such as poor tissue healing, improper implant placement or securement, implant failure, or to patient-related factors. Sometimes revision surgeries are indicated even after successful initial surgeries, given that the function and shape of the spine can deteriorate with age. Also, after prolonged use, the spinal fixation rods may move or become dislodged or unstable, or even bend or break.

Revision surgery is also required to treat adjacent segment disease ("ASD"). Spinal fusion recipients may be at risk for developing ASD, a condition in which the motion segments adjacent to the fused vertebral segments experience higher rates of degeneration or deterioration due to an increase in vertebral loading, higher intradiscal pressures, increased range of motion, and increased facet motion. Treatment options for ASD begin with determining whether the primary fusion is intact. If so, then a revision surgery with a revision connector is a likely course of action.

When considering spinal fusion revision surgery options, a few revision connectors are known, such as the "Revere Addition Revision System" and the "Expedium Universal Connector". However, these connectors suffer from various drawbacks. First, these prior connectors are difficult to connect to the spinal level above the targeted level. This may be due to scar tissue or fusion mass that has developed in the lateral "gutters" across the transverse process. Second, such connectors add significant profile to the implant, both laterally and in height. Increased height can cause problems post-surgery when patients can feel the implants under their skin. Sometimes this leads to deep superficial pain. Third, prior art revision connectors do not achieve adequate stability in-line with the primary rod. Fourth, some prior art connectors are not ideal for minimally invasive surgical implantation techniques.

What is needed is a universal revision connector that is easy to install, with minimal profile, and that can sit in-line, nearly in-line, and/or at desired angles with the primary fusion rod. The connector ideally minimizes the disruption of the previous fusion mass and limposes less violation of the scar tissue. The stabilization may be extended to the next level above or below the fusion. Additional benefit is also achieved with a connector that can be inserted percutaneously. Ideally, a connector is desired that is not only suitable for revision surgeries, but also for primary fusion surgeries. The present connector provides vast improvement over such existing revision connectors.

SUMMARY

The disclosure herein is directed to an apparatus, system, and method for use in primary or revision surgeries. The system or implantable connector system would typically include at least a rotational connector, a connector set screw, a connector rod, and a connector rod set screw in some embodiments. The rotational connector is inserted in a "twist and lock" fashion.

In some embodiments of the invention, for example, an implantable connector system may include a rotational connector. The rotational connector may have a first end and a second end. In some embodiments, the first end may be configured to rotate from a first orientation to a second orientation, wherein in the first orientation the rotational connector may be top loaded onto a head of an existing pedicle screw. In some embodiments, when in the second orientation the first end of the rotational connector may receive an outer surface of a primary fusion rod. The second end may include a receptacle in some embodiments. In various embodiments, the implantable connector system may include a revision rod. The revision rod may have a first end and a second end. The first end may be matingly received in the receptacle of the second end of the rotational connector. Moreover in some embodiments, the implantable connector system may include a connector set screw. The connector set screw may be configured to threadingly engage a set screw opening in the first end of the rotational connector. In various embodiments, the implantable connector system may include a revision rod screw such as a set screw. The revision rod set screw may be configured to threadingly engage a set screw opening in the second end of the rotational connector.

In some embodiments, the rotational connector may include a middle portion top loaded onto a head of an existing pedicle screw. In various embodiments, the rotational connector may include a bottom having a receiving slot configured to receive an existing pedicle screw and a primary fusion rod. Further in some embodiments, the receiving slot may be a vertical first slot intersecting a horizontal second slot. Moreover in some embodiments, the horizontal second slot may be substantially in line with the revision rod when the first end of the revision rod is matingly received in the receptacle of the second end of the rotational connector. In various embodiments, the first end of the revision rod and the receptacle of the second end of the rotational connector may be a ball-and-socket joint. In some embodiments, the first end of the revision rod and the receptacle of the second end of the rotational connector may each have corresponding vertical teeth positioning the revision rod at an angle relative to the rotational connector. Moreover, in various embodiments, the first end of the revision rod or the receptacle of the second end of the rotational connector may include one or more protrusions received in one or more channels of the other one of the first end of the revision rod or the receptacle of the second end of the rotational connector.

In various embodiments, an implantable connector system may include a revision rod. The revision rod may have a first end and a second end. In some embodiments, the implantable connector system may include a rotational connector. Moreover in some embodiments, the rotational connector may have a first end, a second end, and a middle portion connecting the first end and the second end. Further in some embodiments, the middle portion may have a through opening extending from a bottom of the rotational connector. In some embodiments, the rotational connector may have a bottom with a first slot extending inwardly to a second slot. In some embodiments, the second slot may be transverse to and intersects the first slot. In various embodiments, the second slot may extend into the first end of the rotational connector. In various embodiments, the implantable connector system may include at least one first set screw. The first set screw may threadingly engage the first end of the revision rod to the second end of the rotational connector. In various embodiments, the implantable connector system may include at least one second set screw. The second set screw may threadingly engage the first end of rotational connector and extend into the second slot in the first end of the rotational connector.

In addition, in various embodiments, the first end of the rotational connector may include a top member, a bottom member, and a side member interconnecting the top member to the bottom member. In some embodiments the top member, the bottom member, and the side member may define the second slot in the first end of the rotational connector. In some embodiments, the revision rod may be axially aligned with the second slot when the revision rod is coupled with the rotational connector. In various embodiments, the revision rod may not be axially aligned with the second slot when the revision rod is coupled with the rotational connector. Moreover in some embodiments, the revision rod and the rotational connector may be coupled by a ball-and-socket joint. In some embodiments, the second slot may extend into the second end of the rotational connector. In various embodiments, the revision rod may be spaced at a higher elevation than the second slot.

Other embodiments may include a method of implanting a rotational connector. In some embodiments the rotational connector may have a first end and a second end. In various embodiments, the method may include opening a first surgical site in a patient to access a primary fusion site. Moreover, in some embodiments, the primary fusion site may include a primary fusion rod having a longitudinal rod axis and a first end and a second end, and a pedicle screw engaged in a vertebra. The first end of the primary fusion rod may terminate at a first distance away from an outer surface of the pedicle screw measured in a first direction in some embodiments. Further in some embodiments, the first direction may be generally parallel to the longitudinal rod axis. In some embodiments, the method may include inserting the rotational connector in a first orientation through the first surgical site and onto the pedicle screw in a second direction, the second direction may be generally perpendicular to the first direction. In various embodiments, the first orientation may be disposed at an angle to the longitudinal rod axis. In some embodiments, the method may include rotating the rotational connector from the first orientation to a second orientation, wherein in the second orientation the first end of the rotational connector matingly receives therewithin the second end of the primary fusion rod. In some embodiments, the method may include inserting a set screw into the first end of the rotational connector to secure the rotational connector to the primary fusion rod. In various embodiments, the method may include inserting a first end of a revision rod into the second end of the rotational connector. In some embodiments, the method may include inserting a set screw into the second end of the rotational connector to secure the rotational connector to the revision rod.

In addition, in some embodiments, the step of rotating the rotational connector from the first orientation to the second orientation may include wherein in the second orientation the second end of the rotational connector matingly receives therewithin the first end of the primary fusion rod. In various embodiments, the method may include the step of positioning the revision rod at an angle relative to the second end of the rotational connector. Moreover, in various embodiments, the step of position the revision rod at the angle relative to the second end of the rotational connector may include spherical angulation. In some embodiments, the step of rotating the rotational connector from the first orientation to the second orientation may include rotating the rotational connector about a screw head of the pedicle screw after the pedicle screw is inserted into the rotational connector. In some embodiments, the method may include the step of axial alignment of the revision rod and the primary fusion rod. In some embodiments, the step of rotating the rotational connector from the first orientation to the second orientation may include rotating an acute angle between the first orientation and the second orientation. Further, in some embodiments the acute angle may be 30 degrees.

DESCRIPTION OF DRAWINGS

In the drawings, like reference characters generally refer to the same parts throughout the different views. Also, the drawings are not necessarily to scale, emphasis instead generally being placed upon illustrating the principles of the invention FIG. 1 is a top perspective view of an embodiment of a system.

FIG. 2 is a top perspective view of the rotational connector of FIG. 1 illustrating top loading in a first orientation relative to a pedicle screw system.

FIG. 3 is a top perspective view of the rotational connector of FIG. 1 illustrating a second orientation or neutral position relative to the pedicle screw system with the set screws engaging the primary fusion rod.

FIG. 4 is a top perspective view of the rotational connector of FIG. 1 illustrating the top loading of an embodiment of the revision rod.

FIG. 5 is a top perspective view of the revision rod of FIG. 4 illustrating an in-line position of the revision rod fastened by a set screw in the rotational connector.

FIG. 6 is a top perspective view of the rotational connector of FIG. 1.

FIG. 7 is a bottom perspective view of the rotational connector of FIG. 6.

FIG. 8 is a perspective view of the set screw of FIG. 1 for securing the primary fusion rod.

FIG. 11 is a top perspective view of another embodiment of a system, illustrating a rotational connector in a second orientation or neutral position relative to the pedicle screw system with a set screw engaging the primary fusion rod and a revision rod being top loaded onto the rotational connector.

FIG. 12 is a top view of the embodiment of FIG. 11, illustrating a set screw positioning the revision rod at an angle relative to the rotational connector and/or primary fusion rod.

FIG. 13 is a top perspective view of the rotational connector of FIG. 11.

FIG. 18 is top perspective view third embodiment of a system engaging a pedicle screw system, illustrating the rotational connector in the second orientation with the set screw engaging the primary fusion rod removed.

FIG. 19 is top perspective view of the system of FIG. 18 with the set screw of the ball-and-socket engagement of the rotational connector and revision rod exploded away therefrom.

FIG. 20 is a side view of the system of FIG. 18.

FIG. 21 is a side sectional view of the system of FIG. 18 taken along line 21-21.

FIG. 26 is a side view of another embodiment of a system engaging a pedicle screw system.

FIG. 27 is a bottom view of the system engaging a pedicle screw system of FIG. 26.

FIG. 28 is a top perspective view of the system engaging a pedicle screw system of FIG. 26 exploded away from each other.

FIG. 34 is a top perspective view of the system engaging a pedicle screw system of FIG. 33 exploded away from each other.

FIG. 35 is a top view of the system engaging a pedicle screw system of FIG. 33.

FIG. 36 is a side view of the system engaging a pedicle screw system of FIG. 33.

FIG. 37 is a bottom view of the system engaging a pedicle screw system of FIG. 33.

FIG. 39 is a top perspective view of the system engaging a pedicle screw system of FIG. 38 exploded away from each other.

FIG. 40 is a top view of the system engaging a pedicle screw system of FIG. 38.

FIG. 41 is a side view of the system engaging a pedicle screw system of FIG. 38.

FIG. 42 is a bottom view of the system engaging a pedicle screw system of FIG. 38.

DETAILED DESCRIPTION

Figure 9:
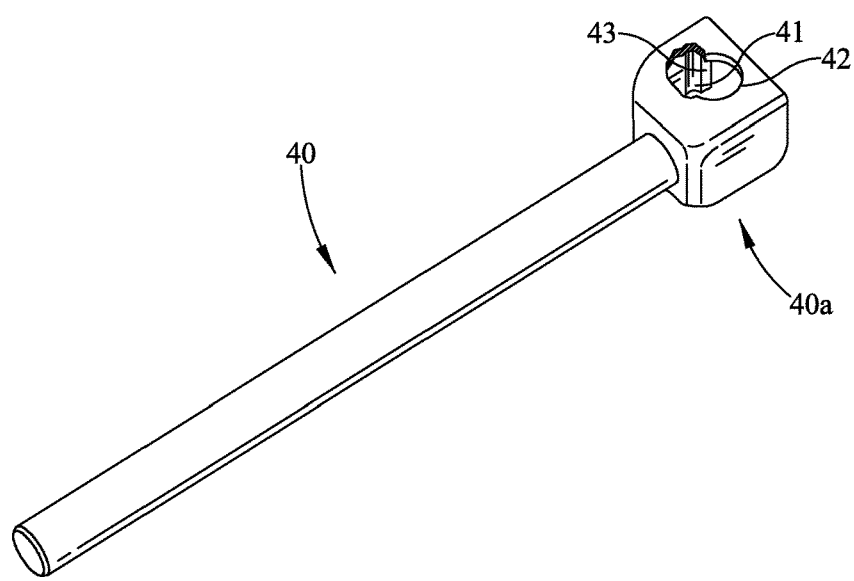
FIG. 9 is a perspective view of the revision rod of FIG. 1.
Figure 10:
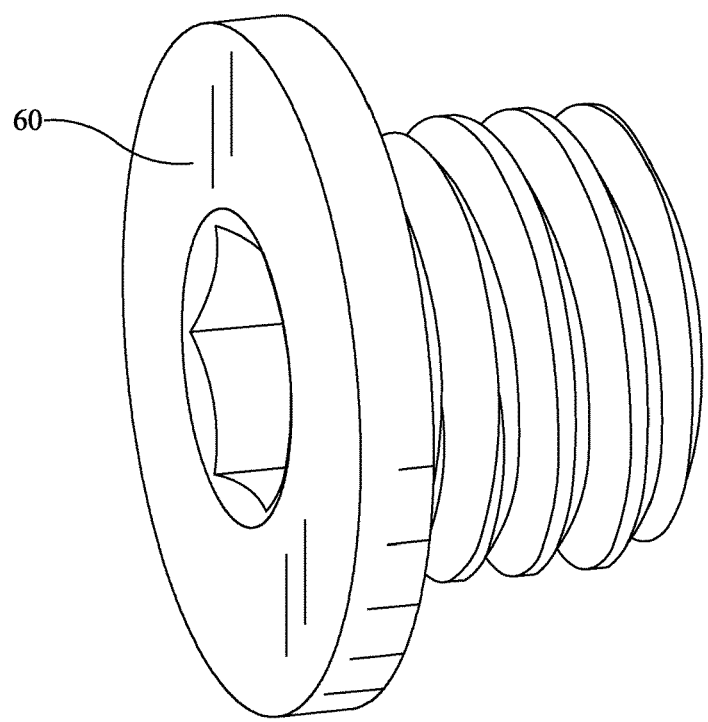
FIG. 10 is a perspective view of the connector rod set screw of FIG. 3 for securing the revision rod.

FIG. 1 shows a first embodiment of the implantable connector system 20 and/or rotational connector 30. In the embodiments described herein, the context of a revision surgery will be used as an example, it being understood that the principles, methods, and structures involved are equally suited in the context of primary surgery as well. For example, in the context of a revision surgery, the embodiments describe the rod that is connected to the "primary fusion rod" to be a "revision rod". However, in primary fusion surgeries using the apparatus herein, the "revision rod" is more generically referred to as a secondary fusion rod.

In a first embodiment as shown in FIGS. 1-10, the apparatus includes a top-loading, rotatable, in-line rotational connector 30 for coupling a revision rod 40, or secondary rod, to a primary (pre-existing, if in a revision surgery) fusion rod 2 of a pedicle screw system 1. The rotational connector 30 is a top loaded "twist connect" design that fits over an existing pedicle screw 3, or more specifically in some embodiments the screw head, and then twists into an in-line position (FIG. 3) with a first end 30a of the rotational connector 30 cradling an end 2a of an existing primary fusion rod 2. The rotational connector 30 is then secured to the end 2a of the primary fusion rod 2 with one or more set screws 50. A first end 40a of a revision rod 40 is then inserted into the second end 30b of the rotational connector 30, and secured with one or more set screws 60.

As shown in the embodiment of FIGS. 1-10, the rotational connector 30 may include a receiving slot 31 to engage the pedicle screw 3 and the primary fusion rod 2. In the embodiment shown, the receiving slot 31 may include a first slot 32 intersecting a second slot 33 to receive the pedicle screw 3 and the primary fusion rod 2. The first slot 32 may extend upwardly from a bottom 34 of the rotational connector 30 for a first distance allowing the screw head 4 and primary fusion rod 2, on one or both sides of the screw head, to be received within the first slot 32 of the rotational connector 30 when in the first orientation (FIG. 2). The screw head 4 and/or primary fusion rod 2 may be substantially vertically inserted into the first slot 32 for the first distance. As such the rotational connector 30 may be vertically coupled to the screw head 4 and/or the primary fusion rod 2 when in the first orientation (FIG. 2). The first slot 32 may be described in some embodiments as being in a substantially vertical first plane P1. The second slot 33 is transverse to and intersects the first slot 32 (i.e. perpendicular to the first slot). The second slot 33 may be described as being in a second plane P2 transverse to the first plane. The second slot 33 may extend within the second plane P2 from the first plane P1 or first slot 32 passing through the central axis C of the rotational connector 30, (i.e. the central axis of the screw head 4), and may extend in opposite rotational angles A from the first plane P1 about the central axis C. The second slot 33 and/or first slot 32 do not have to be symmetric and/or similar in shape or size (length, width, and/or height) about the central axis C in some embodiments. For example although the second slot 33 is shown as extending through both rotational connector ends from the central axis C and/or portions of the first slot 32, it should be understood that that second slot may not extend into the second end 30*b* in some embodiments such as when the primary fusion rod is not present or of a reduced distance/length on one side of the screw head 4 adjacent the revision rod 40. The second slot 33 may be generally described as increasing in width along the second plane P2 in opposing directions from the central axis C, or towards the first end 30*a* and opposing second end 30*b* of the rotational connector 30. The second slot 33 may extend through opposing lateral sides 35, 36 of the rotational connector 30, thereby creating open faces at the respective first end 30*a* and second end 30*b* of the rotational connector 30. When the rotational connector 30 has been vertical positioned (i.e. downwardly) for a the first distance within the first slot 32 in the first orientation (FIG. 2), these open faces or openings adjacent one or more of the connector ends allow the primary fusion rod 2 projecting from the screw head 4 in at least one direction to pass through and continue into the remaining portion of the second slot 33. As such, at least the primary fusion rod 2 travels or rotates within the second slot 33 for a second distance or angle on one or both sides of the screw head 4 and/or middle portion 30*c*. Thereby when positioning the rotational connector 30 from the first orientation (FIG. 2) to the second orientation (FIGS. 1 and 3-5), the rotational connector 30 further rotates for an angle A relative to the primary fusion rod 2 and the screw head 4 traveling within the second slot 33. It should be understood that one or more slots may be used to vertically insert and/or rotate the rotational connector 30 relative to the pedicle screw 3 and/or primary fusion rod 2. For example, a helical slot extending upwardly from the bottom 34 of the rotational connector may provide for the vertical and rotational movement of the rotational connector relative to the pedicle screw and rod.

The rotational connector 30 may include a variety of structure to define the receiving slot 31 that allows axial and rotational engagement with the pedicle screw system 1 between the first orientation and second orientation (i.e. screw head 4 and primary fusion rod 2). In the embodiment shown in FIGS. 1-10, the rotational connector 30 may include a first end 30*a*, second end 30*b*, and a middle portion 30*c* between the first end 30*a* and second end 30*b* in some embodiments. The middle portion 30*c* may include a cylindrical wall defining a through opening 37 to receive or slip over a top portion of the screw head 4. The through opening 37 may be a portion of the first slot 32 and/or second slot 33. The first end 30*a* and second end 30*b* project in opposing directions from the outer periphery of the wall of the middle portion 30*c*. The first end 30*a* of the rotational connector 30 receives an outer surface of the primary fusion rod 2. The first end 30*a* may be generally described as U-shaped or a C-channel extending from the middle portion 30*c*. The first end 30*a* of the rotational connector includes a top member 38*a* and bottom member 38*b* connected by a side member 38*c*. The top and bottom members 38*a*, 38*b* are separated by the second slot 33 and define the open face of the first end 30*a* within the lateral side 36. In some embodiments, the bottom member 38*b* may include a tapered edge 38*d* defining the first slot 32 for substantial vertical insertion from the bottom 34. The open face extends from the lateral side 36 to a distal free end 38*e*. The side member 38*c*, opposite the open face, may be an abutment to the primary fusion rod 2 in its neutral position in the second orientation (FIG. 3) of the rotational connector 30. The first end 30*a* of the rotational connector 30 may include one or more set screw openings 50*a*, 50*b*. In the embodiment shown, the top member 38*a* of the first end 30*a* includes one or more set screw openings 50*a* and 50*b* to receive one or more connector set screws 50. The connector set screws 50 may compress the primary fusion rod 2 against the bottom member 38*b* to secure the rotational connector 30 in the second orientation. The second end 30*b* of the rotational connecter 30 may couple adjacent ends of the primary fusion rod 2 and the revision rod 40. The second end 30*b* of the rotational connector 30 may include a receptacle 70 configured to receive a first end 40*a* of the revision rod 40. On embodiment of the receptacle 70 of the second end 30*b* opposite the first end 30*a* may include a top member 71 and a depending side member 72. The top member 71 and/or side member 72 may define a portion of the second slot 33 and the open face in the opposite facing direction or lateral side 35 of the first ends' open face on the lateral side 36. The open face extends from the lateral side 35 to the distal free end 73 in some embodiments. The open faces of the first and second ends 30*a* and 30*b* face in the same rotational direction (i.e. clockwise direction), towards the second orientation. The side member 72 of the second end 30*b* may be a rotational stop of the primary fusion rod 2, if the side member and/or primary fusion rod end is present. In some embodiments, side members 72 may not be used or saddle the primary fusion rod. Further in some embodiments, the middle portion 30*c* and the first end 30*a* may define the receiving slot 31 to receive the screw head 4 and primary fusion rod 2 therein (see FIGS. 26-42). Although not shown, a bottom member may be used in the second end 30*b* if desired. In some embodiments, the second end 30*b* may not include a portion of the second slot 33 and/or receiving slot 31. The one or more lateral sides 35 and 36 of the second end 30*b* or receptacle 70 may include a protrusion 74, or alternatively a recess in some embodiments, to interlock with a revision rod 40 in some embodiments. The interlocking of the second end 30*b* or receptacle 70 (i.e. outer periphery and/or inner periphery) and the revision rod 40 may reduce separation. In the embodiment shown, the protrusion 74 is a vertical rib projecting from each lateral side 35, 36 of the second end 30*b*. As such the revision rod engagement would have a corresponding engagement feature. The revision rod 40 in the embodiment shown in FIGS. 1, 4, 5, and 9 may include a vertical recess or channel 41 to slidingly receive the vertical rib or protrusion 74 of the rotational connector 30. The second end 30*b* of the rotational connector 30 may include one or more set screw openings 60*a* to receive a revision rod set screw 60 to couple the revision rod 40 to the rotational connector 30. The first end 40a of the revision rod includes an opening 42 receiving the revision rod set screw 60. In the embodiment shown, the top member 71 of the second end 30b includes the set screw opening 60a.

As shown in FIGS. 1, 4, 5, and 9, the revision rod 40 may couple to the second end 30b of the rotational connector 30. As shown in the embodiment of FIG. 1, the first end 40a of the revision rod 40 couples to the second end 30b or receptacle 70 of the rotational connector 30. The first end 40a of the revision rod 40 includes an inner periphery 43 sliding over the outer periphery of the second end 30b of the rotational connector 30. The revision rod set screw 60 threadingly engages the revision rod 40 to the second end 30b of the rotational connector 30. When the rotational connector 30 is in the second orientation, the revision rod 40 is substantially aligned. In the embodiment shown in FIG. 5, the revision rod 40 may be substantially co-axial (i.e. substantially vertically and horizontally aligned with the primary fusion rod 2). It should be understood that a variety of embodiments of the rotational connector 30, receptacle 70, and/or revision rod 40 may be used to orientate and/or position the revision rod in a variety of angles and/or heights relative to the rotational connector 30 for a particular application. It should also be understood that the receptacle 70 engaging the revision rod 40 may be of a variety of shapes, sizes, quantities, and constructions and still position the revision rod for an application.

The rotational connector 30 may be described as having a "twist connect" design. The rotational connector 30, or more specifically the middle portion 30c, is adapted to fit a variety of screw sizes. The through openings 37 may be sized in diameter and/or height to correspondence to a variety of screw head 4 or pedicle screw 3 designs. The height of the rotational connector 30 may not extend vertically above the existing screw head in some embodiments. Moreover, the revision rod may not extend above the vertical extent of the rotational connector, or portions thereof. In the embodiment shown in FIGS. 2-5, the first end 40a of the revision rod 40 is received in a recessed or lower surface 75 of the second end 30b creating a substantially planar top surface of the combined revision rod 40 and rotational connector 30. The recessed surface 75 may include the top member 71 at a lower elevation than the top surface of the middle portion 30c. When combined as shown in FIG. 5, the revision rod 40 is substantially in line with the existing primary fusion rod 2. The rotational connector 30 may allow the revision rod 40 to be inserted sub muscularly in some embodiments. The rotational connector is top loaded onto the pedicle screw (i.e. vertical movement) (see FIGS. 2 and 3). The rotational connector 30 may be rotated from a first orientation (FIG. 2) wherein the screw head is engaged at a vertical or down position and the primary fusion rod 2 is disengaged to a second orientation (FIG. 3) wherein the screw head 4 and one or more of the opposing ends of the primary fusion rod 2 extending away from the screw head is engaged. The rotational connector 30 may be placed by rotating an acute angle between the first orientation to the second orientation. In some embodiments, the angle may be a variety of angles between the orientations (i.e. obtuse angle). In the embodiment shown, the rotational connector 30 travels about 30 degrees between the first orientation and the second orientation. When the rotational connector is rotated to the second orientation, or neutral position, one or more set screws 50 may lock the rotational connector 30 to the primary fusion rod 2. The revision rod 40 may be top loaded upon rotational connector 30 and axially aligned with the primary fusion rod 2 and secured to the rotational connector 30 by one or more screws 60. The revision rod 40 may not be axially aligned in some embodiments.

The end of the existing fusion rod can protrude beyond the pedicle screw in a range of distances, which are typically not known ahead of time since it was a result of the previous surgeon's work. The rotational connector herein is designed to be placed in-line over the existing rod with enough room to accommodate for nearly any amount of protrusion by the existing rod. Typically surgeons like to leave at least some amount of rod protruding beyond the screw to ensure that there is a guarantee that the rod is completely in the saddle of the screw for grip strength. The rotational connector herein is designed so that surgeons never need to adjust the pre-existing rod or construct because the goal is to leave the original fusion rod/construct untouched if possible, to minimize the risk of compromising fusion, as well as to eliminate the need to simply replace the existing fusion rod construct and the screws at the existing level when proceeding to build up to the next levels during revision surgery.

The revision rod can be as long as desired. Theoretically, the surgeon could run the revision rod all the way up the spine if desired, though this would not be typical. Usually, surgeons will elect to cut the revision rod to the desired length during revision surgery; thus, the revision rod herein can begin as long as desired, and then can be cut by the surgeon.

The set screws are prevented from backing out via their standard, well-known set screw thread design. This is the same mechanical principle that applies to a pedicle screw with a locking set screw: once a recommended torque on the set screws is achieved, the set screws are secure.

In this first embodiment shown in FIGS. 2-4, 6, and 7, one or more ridges, tongues, or protrusions 74 are provided on the external surface of the second end 30b of the rotational connector 30. These protrusions 74 mate with corresponding grooves inside the first end 40a of the revision rod head portion. These protrusions 74 are designed to interface to carry the load between the two components. This way the set screw 60 does not have to sustain the full load in some embodiments. In other embodiments they could be replaced by a single spherical surface (as, e.g., in a second embodiment described below) or by a rod that has a female spherical ball end that drops into a mating spherical cavity of the rotational connector shown and described in an embodiment below. The purpose of these alternatives is to prevent separation and allows the rod to be angulated in order to accommodate less than perfectly placed pedicle screws. This allows for a more secure connection while allowing for some variation in placement.

The rotational connector 30 that accepts the existing rod is designed to have a geometric shape that adds structural stability to the rotational connector as shown in FIG. 3. The material of the rotational connector 30 creates a tall wall or side member 38c on one side of the existing rotational connector 30. The rotational connector can accept most commonly used rods (such as, e.g., 5.5 mm rods), but obviously can be easily dimensioned to fit on larger or small diameter rods as desired. The rotational connector itself has an inner diameter and surface that defines the through opening 37 and accommodates the many sizes of pedicle screws used by many manufacturers throughout the years.

The rotational connector 30 can be inserted into a patient in a standard open procedure, or can be inserted submuscularly or percutaneously. In this fashion, the rotational connector 30 can be categorized as an MIS connector.

As shown in FIG. 2, in one embodiment for one example application (spinal fusion revision surgery), the rotational connector 30 fits around the head of an existing, previously implanted screw, and then rotates into an in-line position with an existing, previously implanted fusion rod. The rotational connector 30, at the angle of the first orientation, slides over the screw head 4 vertically to a position or down position within the first slot 32 of the receiving slot 31 and subsequently rotates within the second slot 33 of the receiving slot 31 to the second angle of the second orientation.

Several options are used to accommodate pedicle screws 3 from various manufacturers, including multiple sizes of through openings 37 in the rotational connector in order to ensure a tight fit therearound.

Figure 14:
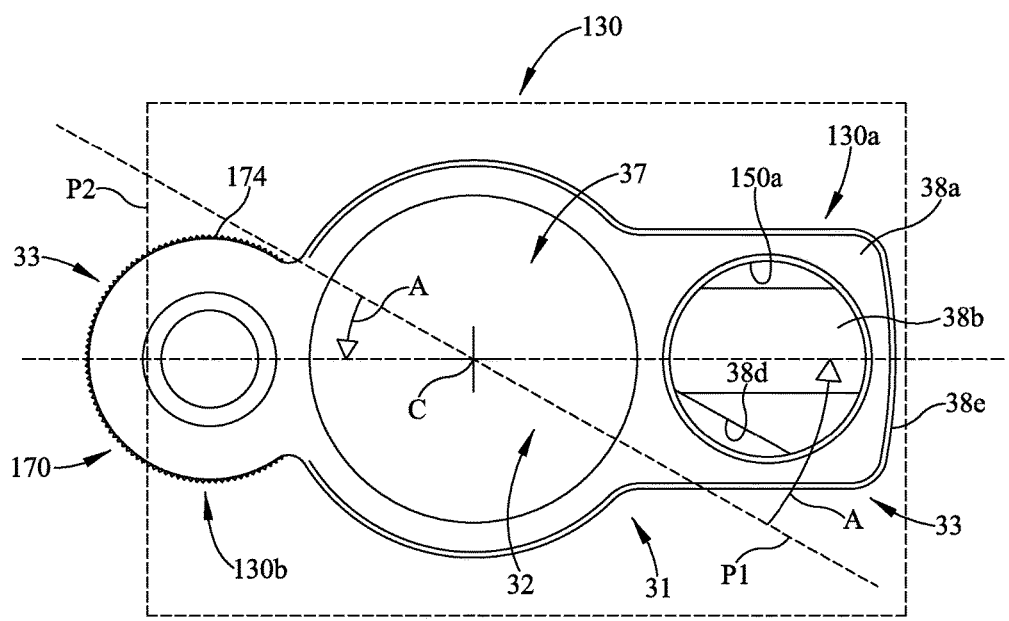
FIG. 14 is a top view of the rotational connector of FIG. 13.
Figure 17:
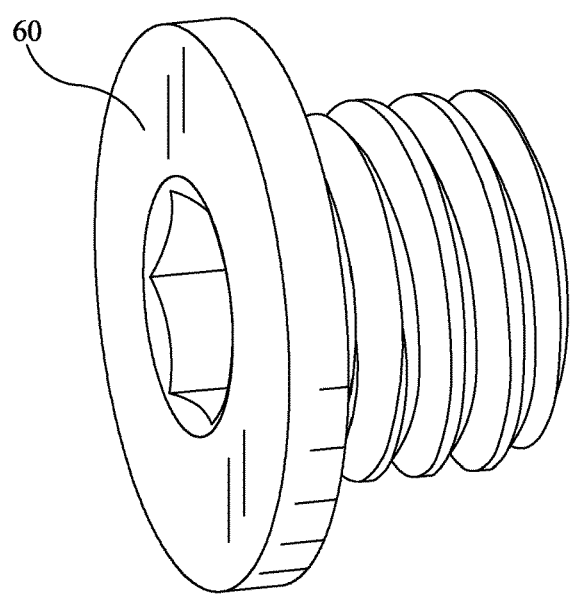
FIG. 17 is a perspective view of the set screw for the revision rod of FIG. 11.
Figure 22:
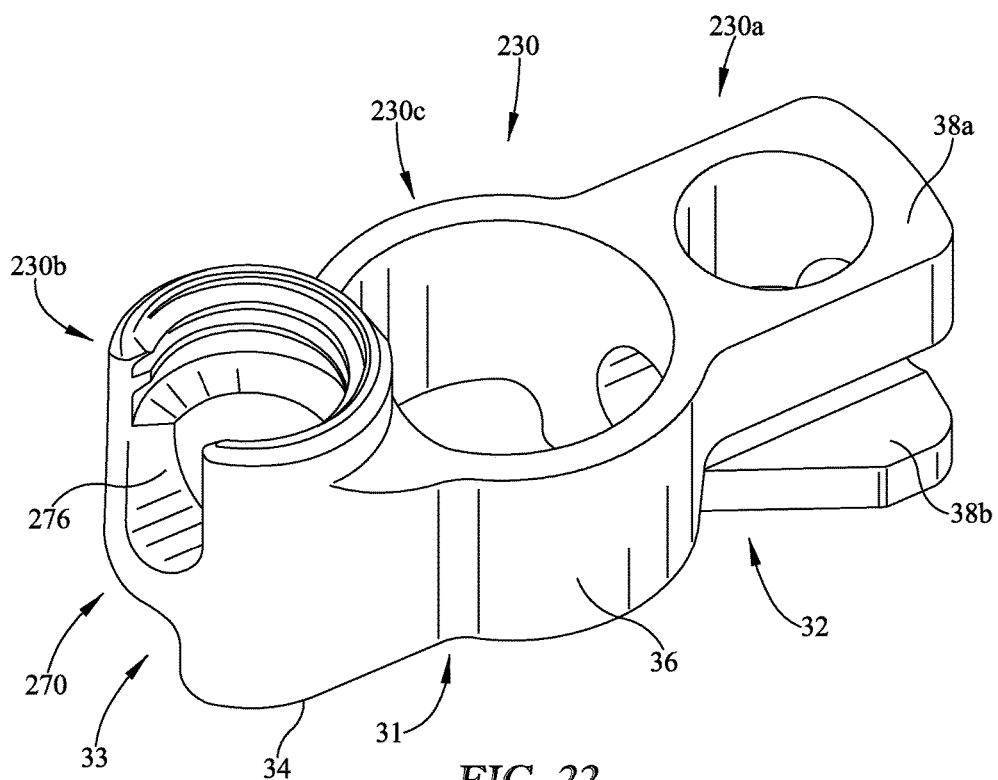
FIG. 22 is a top perspective view of the rotational connector of FIG. 18.
Figure 23:
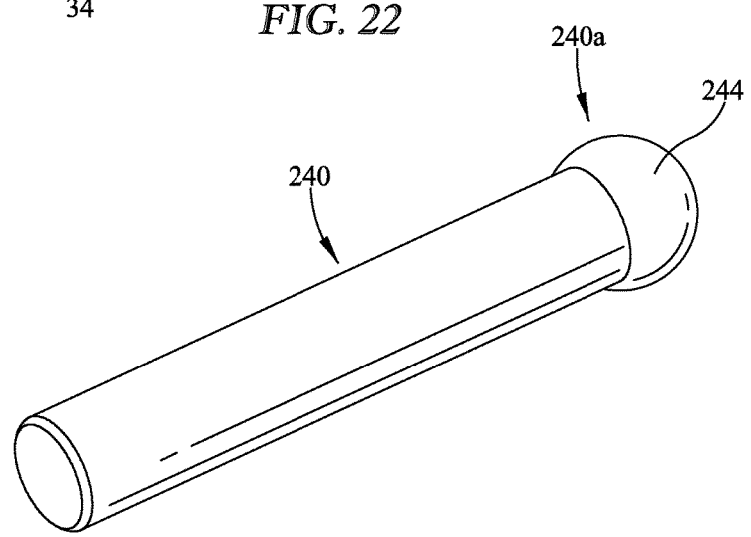
FIG. 23 is a perspective view of the revision rod of FIG. 18 for use with the rotational connector.
Figure 24:
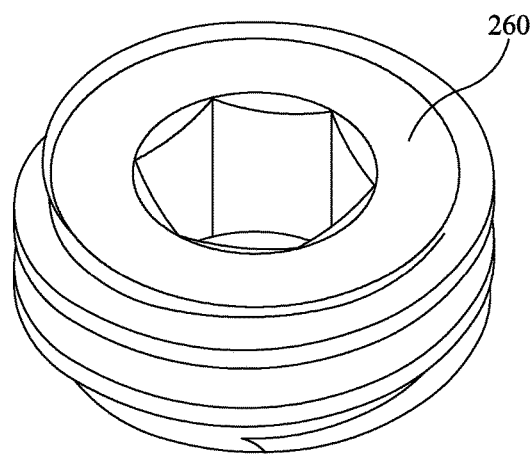
FIG. 24 is a perspective view of the set screw of FIG. 18 for engaging the revision rod.

In a second embodiment show in FIGS. 11-17, the implantable connector system 120 may provide adjustability for the relative angle of the revision rod 140 relative to the rotational connector 130. Another embodiment of the second end 130b of the rotational connector is shown in FIGS. 11 and 14. The rotational connector 130 includes external serrations or teeth 174 on the outer surface of the revision rod receiving end or receptacle 170. The second end 130b includes external vertical serrations 174 on the outer periphery (i.e. the lateral sides and interconnecting distal free end). The outer periphery of the second end 130b may by arcuate in shape. The first end 140a of the revision rod may have a corresponding shape to engage the second end 130b. The inner periphery of the first end 140a of the revision rod 140 includes serrations 141 at least in the upper portion of the cavity. The corresponding serrations 141 and 174 between the structures may interlock or interfere with relative rotation therebetween. In the embodiment shown in FIG. 12, when the revision rod 140 is positioned at the desired angle B relative to the second end 130b of the rotational connector 130, the revision rod is vertically coupled. The revision rod set screw 60 as shown in FIG. 17 is then threadingly engaged. The revision rod 140 may be in substantially the same horizontal plane of the primary fusion rod 2 and still be a variety of angular positions (i.e. angle B) relative to the second end 130b of the rotational connector 130. Moreover, the rotational connector 130 includes another embodiment of the first end 130a. The first end 130a of the rotational connector 130 includes a single set screw opening 150a for threadingly engaging a corresponding connector set screw 150.

Any number and type, size, and design of serrations 174 are possible. These serrations 174 allow a surgeon to place the revision rod 140 at an angle B with respect to the pre-existing fusion rod 2. While the figures shows an example angle B of ten degrees per side, this is just an example, and any number of angles are possible from zero to approximately 90 degrees per side, depending on the fit between the revision rod 140 and the rotational connector 130, and where the construct is to be implanted in the patient. The rounded second end 130b of the rotational connector 130 may allow for medial/lateral revision rod 140 rotation.

Figure 15:
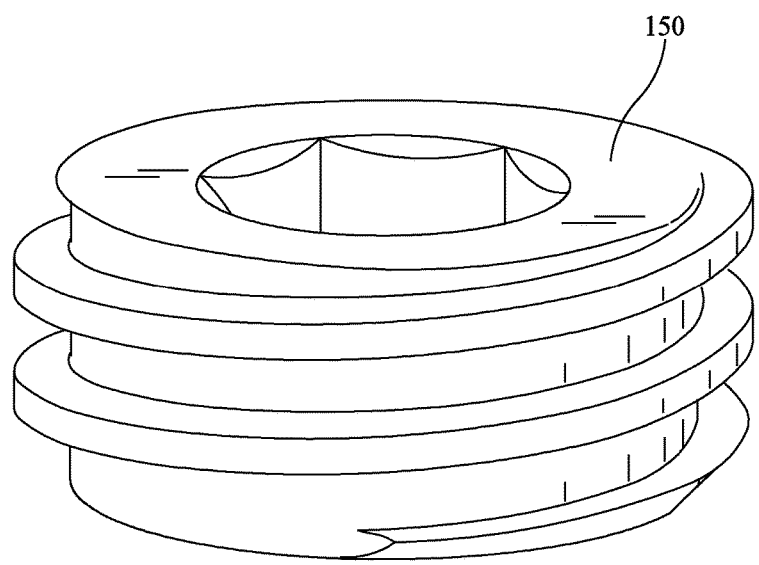
FIG. 15 is a perspective view of the set screw for the rotational connector of FIG. 11 for engaging the primary fusion rod.
Figure 16:
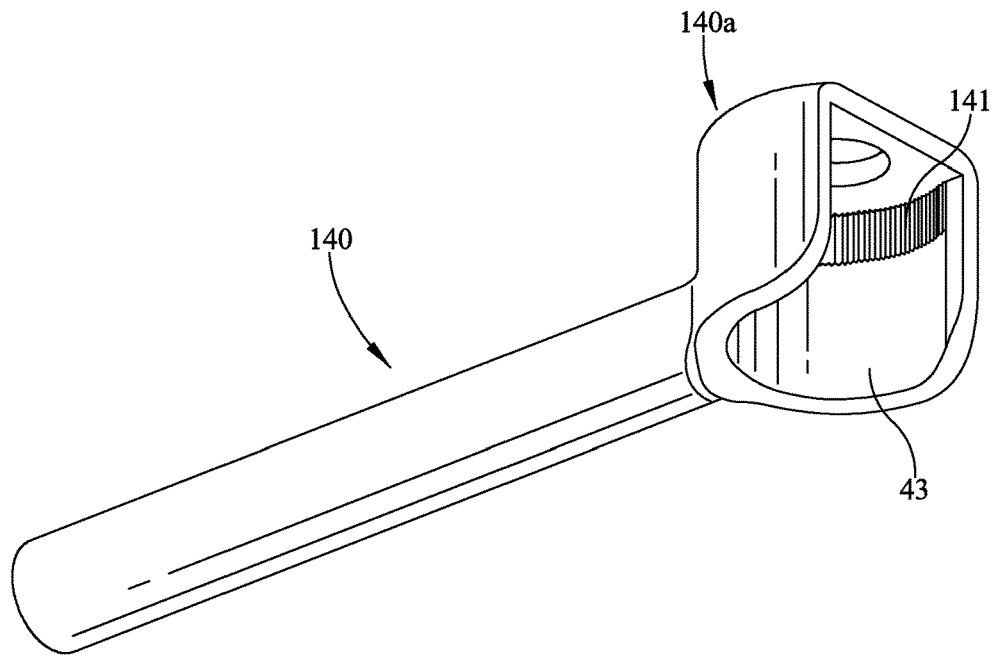
FIG. 16 is a bottom perspective view of the revision rod of FIG. 11 for use with the rotational connector opposite the primary fusion rod.

In this embodiment, as in all the embodiments, any number of set screws or screws can be utilized, depending on the size and shape of the construct required. Often, surgeons desire the smallest profile possible from an implant that does not compromise strength. In some embodiments as shown in FIGS. 12 and 15, a single larger set screw 150 will have a smaller profile than two set screws 50 of FIG. 3, for example.

In a third embodiment of the implantable connector system 220 shown in FIGS. 18-24, another engagement between a revision rod 240 and rotational connector 230 may be used in a variety of applications. The rotational connector second end 230b or receptacle 270 that receives the first end 240a of the revision rod 240 is fitted with a socket 276 to receive a "ball" end 244 of the revision rod 240, as shown in FIGS. 19 and 21. As shown in this embodiment, the second end 230b or receptacle 270 of the rotational connector 230 may position the first end 240a of the revision rod 240 in a different vertical position or another horizontal plane relative to the primary fusion rod 2. However, the adjacent ends of the rods 240 and 2 may be substantially in the same horizontal plane, or along the longitudinal axis, of the rotational connector 230 in some embodiments (See FIG. 25). The top surface of the second end 230b of the rotational connector 230 may be at a higher elevation or horizontal plane relative to the remaining portions of the rotational connector (i.e. middle portion 230c and/or first end 230a). For example, the top surface of the second end 230b may be 0.2 inches or 5 mm above top surface of the middle portion 230c of the rotational connector in some embodiments.

In the embodiment shown in FIGS. 18-24, angulation of the revision rod 240 can be achieved via the ball-and-socket joint, 276 and 244. Once the desired angle is achieved by the surgeon, a revision rod set screw 260 is tightened against to hold the angle. This is akin to the polyaxial nature of many pedicle screws; here the set screw contacts the spherical head of the revision rod directly. There may be increased strength (i.e. torsion, F/E, compression) between the revision rod interface. Moreover, the spherical angulation between the revision rod 240 and the rotational connector 230 may increase variability and ease of insertion with adjacent levels.

Other options exist for achieving, and then holding, the desired angulation, including the use of compression collets around the spherical head of the revision rod, as described in commonly owned U.S. Pat. No. 8,197,517, the disclosure of which is incorporated by reference herein. Such a friction collet provides a means to grip and secure the rod at the desired position once placed and the set screw is tightened to the recommended tightening torque. Another option is the use of a set screw that is integrally formed within a body that has a saddle-shaped blocking mechanism. The saddle has a post at its central axis around which the set screw rotates. The saddle block could be designed to lock certain angulations. For example, one saddle might be a zero angle saddle, wherein each side of the saddle is of equal size and shape, and it fits down over the revision rod. A different saddle might have one "leg" larger or thicker than the other, which would lock in a particular angle. Another option is having the bottom of the locking set screw for the rod have a spherical underbody with spherical shaped ridges to increase grip strength to secure the rod in position once placed. This locking set screw has a spherical cavity much like the concept of the collet.

Figure 25:
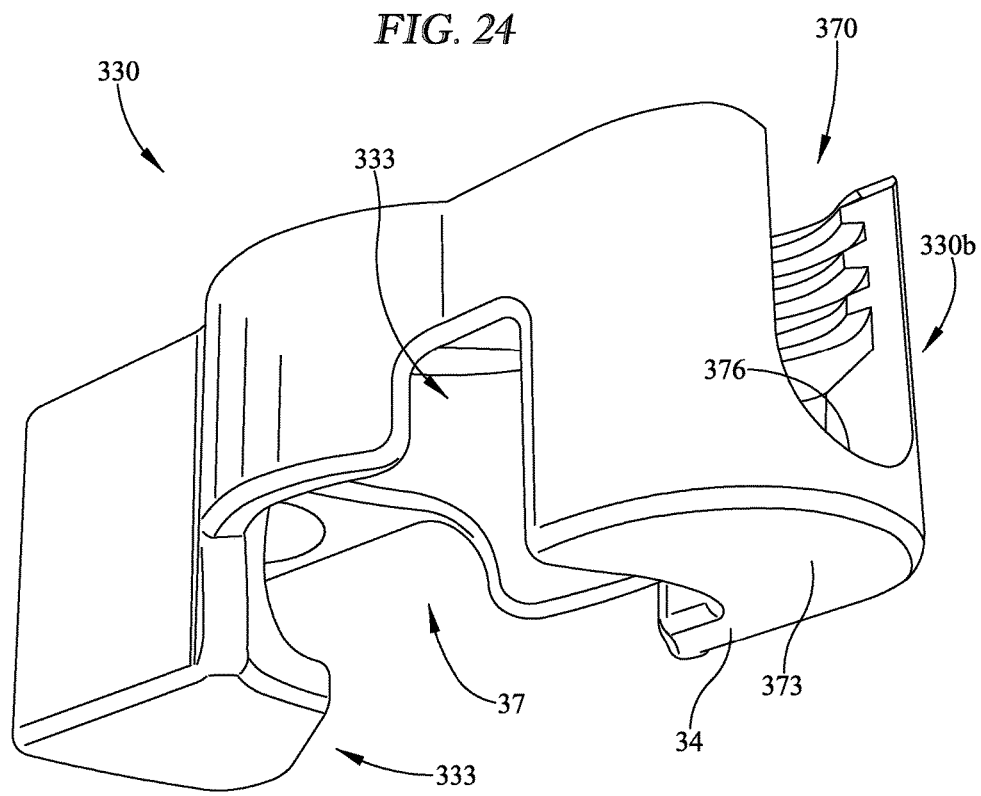
FIG. 25 is a bottom perspective view of a fourth embodiment of a rotational connector.
Figure 29:
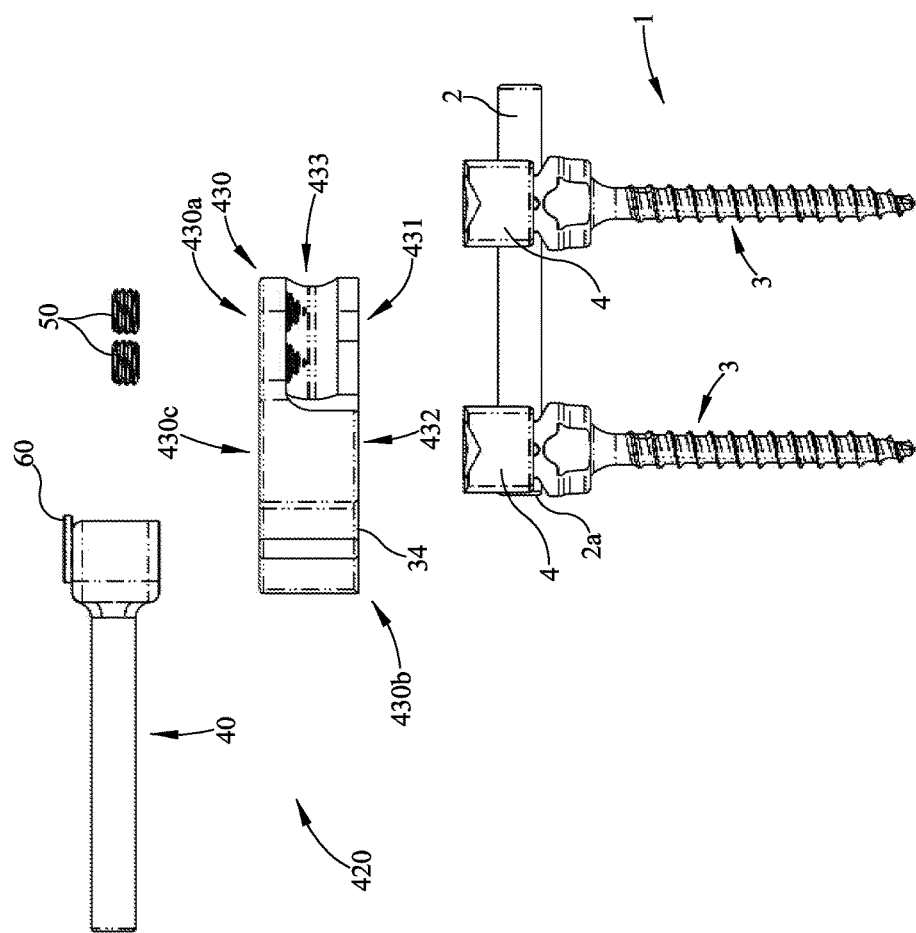
FIG. 29 is a side view of FIG. 28.
Figure 30:
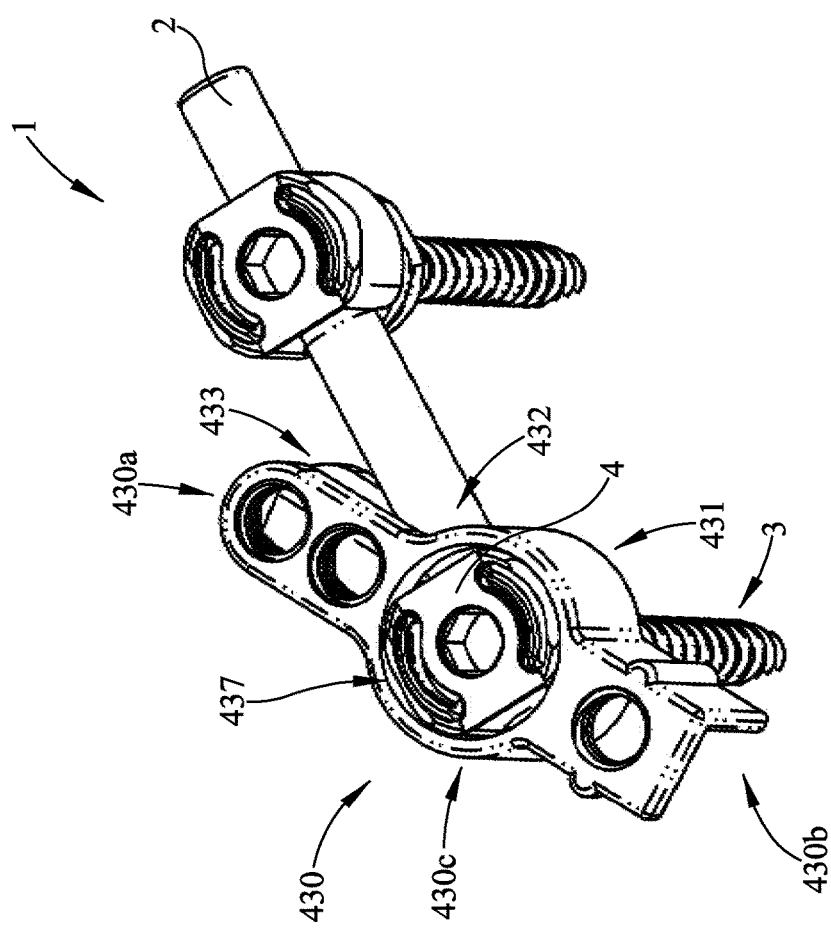
FIG. 30 is a top perspective view of the rotational connector of FIG. 26 in a first orientation relative to the pedicle screw system.

Another embodiment of the rotational connector 330 is shown in FIG. 25. The rotational connector 330 may include an embodiment of a second end 330b that positions the first end 240a of the revision rod substantially in the same horizontal plane, along the longitudinal axis, of the rotational connector or primary revision rod 2. The revision rod may be axially aligned with the second slot or primary fusion rod in some embodiments. The receptacle 370 or ball-and-socket joint (i.e. socket 376) may be adjacent the end of the primary fusion rod or lower in elevation than the ball-and-socket joint in FIG. 20. Another embodiment of the second end 330b as shown in FIG. 25 includes a distal free end 373 that may cover at least a portion of the axial end of the primary fusion rod 2. As such the second slot 333 may not extend through the distal free end 373 of the second end 330*b* in some embodiments. The inside surface of the distal free end 373 may abut against the axial end of the primary fusion rod 2 or be spaced from the inside surface of the distal free end 373.

Figure 31:
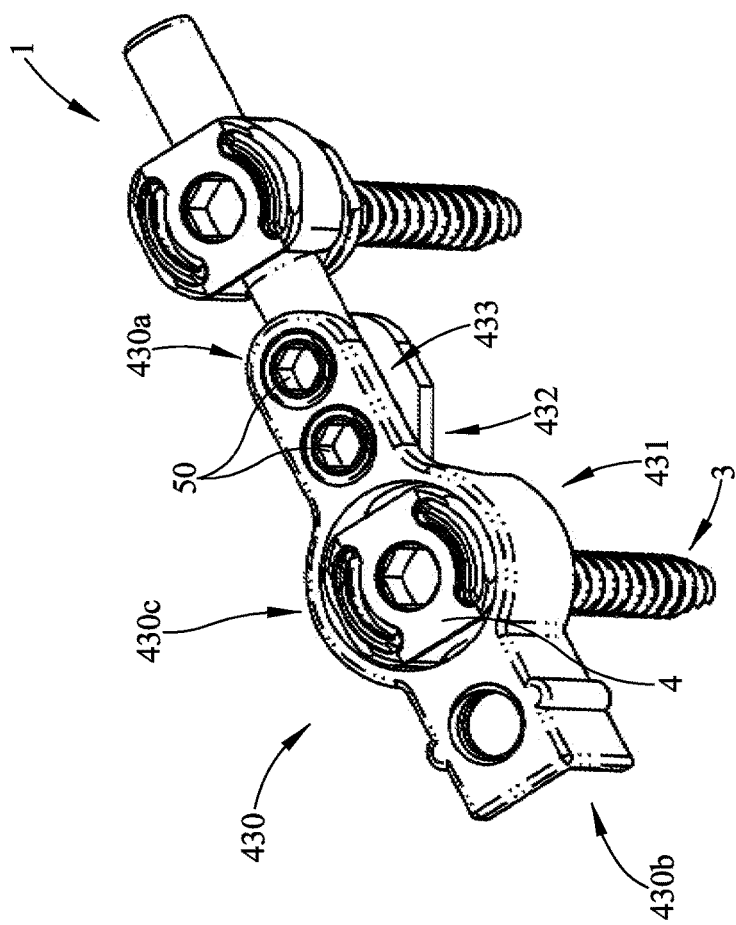
FIG. 31 is a top perspective view of the rotational connector of FIG. 26 in a second orientation relative to the pedicle screw system illustrating the set screws engaging the primary fusion rod.
Figure 32:
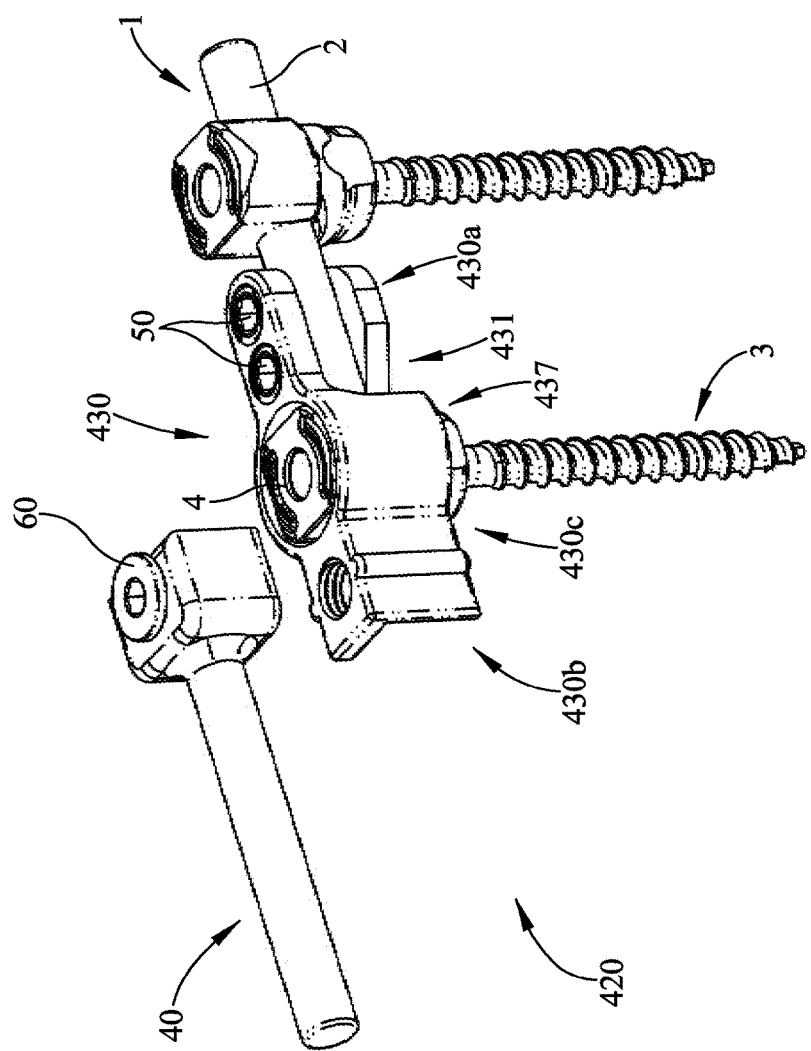
FIG. 32 is a top perspective view of the rotational connector of FIG. 26 in a second orientation relative to the pedicle screw system illustrating the top loading of the revision rod.
Figure 33:
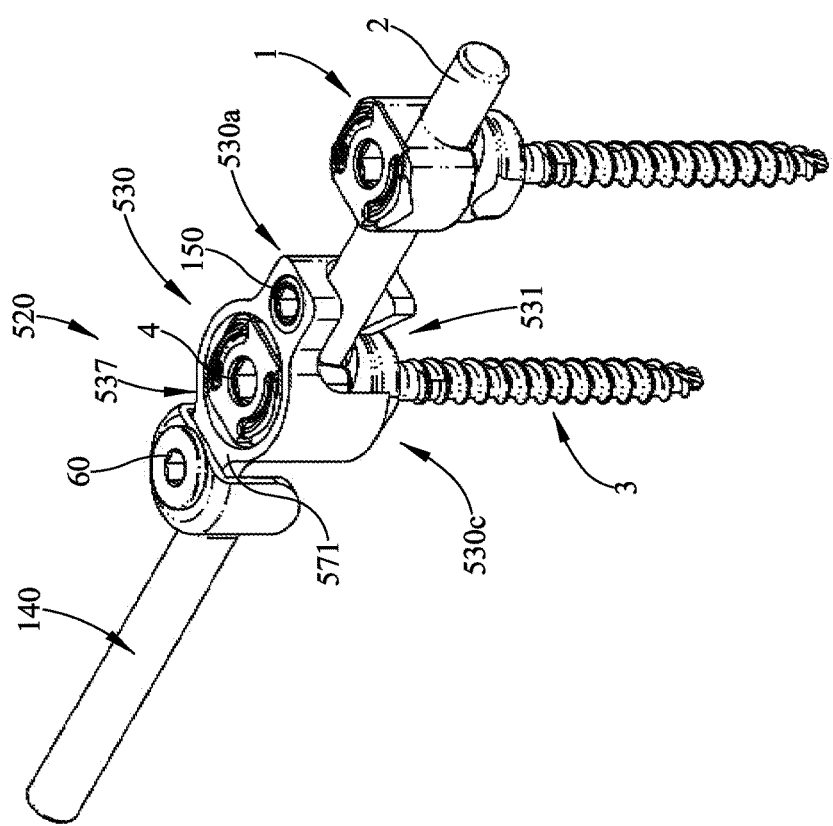
FIG. 33 is a top perspective view of another embodiment of a system engaging a pedicle screw system.
Figure 38:
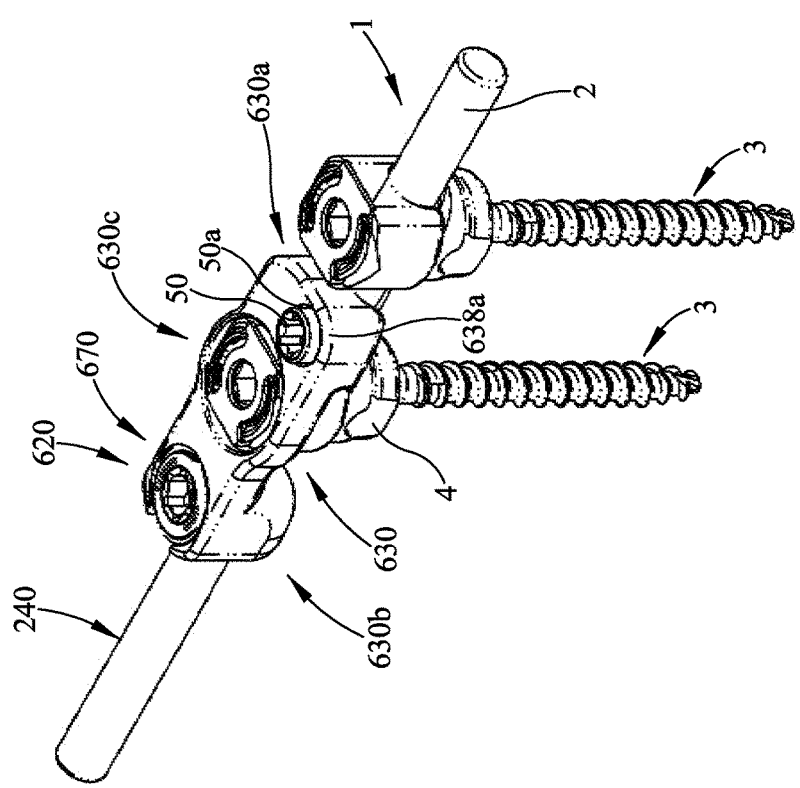
FIG. 38 is a top perspective view of another embodiment of a system engaging a pedicle screw system.

Another embodiment of the implantable connector system 420 is shown in FIGS. 26-33. The rotational connector 430 includes a receiving slot 431 not extending through the second end 430*b*. The first and second slots 432 and 433 extend upwardly into the middle portion 430*c* and the first end 430*a*. The through opening 437 may be enclosed by the wall of the middle portion 430*c*. Therefore the end of the primary fusion rod 2 may not extend radial past the through opening 437 from the screw head 4 to allow the rotation of the rotational connector 430 from the first orientation (FIG. 30) to the second orientation (FIGS. 31-33). Moreover in the embodiment shown in FIG. 26, the top surface of the second end 430*b* is substantially planar with the top surface of the middle portion 430*c*. As best shown in FIGS. 26 and 27, the second end 430*b* positions the revision rod 40 in a spaced elevation, or different horizontal plane, from the axis of the primary fusion rod 2. However it should be understood that a recessed surface 75 may be used with this embodiment. If a recess is used in an embodiment the revision rod 40 may be horizontally and vertically aligned with the primary fusion rod 2.

Another embodiment of the implantable connector system 520 is shown in FIGS. 34-37. Generally similar to the embodiment of the implantable connector system 120, however the rotational connector 530 includes a receiving slot 531 not extending through the second end 530*b*. The first and second slots 532 and 533 extend upwardly into the middle portion 530*c* and the first end 530*a*. The through opening 537 may be enclosed by the wall of the middle portion 530*c*. The second end 530*b* does not include a sidewall depending from the top member 571 with serrations 574. Moreover in this embodiment, the second end 530*b* does not include a recessed surface 75 as in FIG. 3. However, a recess may be used. As shown in FIGS. 33 and 35, the revision rod 140 is positioned at an angle B, being zero degrees in the application shown.

Another embodiment of the implantable connector system 620 is shown in FIGS. 38-42. The rotational connector 630 includes a receptacle 670 positioning the revision rod 240 substantially in line with the primary fusion rod 2. The receptacle 670 of the second end 630*b* includes a ball-and-socket joint as described above. The receptacle 670 is substantially in line with the primary fusing rod 2, similar to the embodiment in FIG. 25. Further, the first end 630*a* of the rotational connector 630 illustrates a single set screw 50 being used. Although two or more set screws are contemplated. The set screw 50 and/or opening 50*a* is offset within the top member 638*a* from the axis of the primary fusion rod 2 or spaced from the side member 638*c*. Moreover, the set screw 50 is not positioned over the bottom member 638*b*. Stated alternatively, the first and second slots 632 and 633 of the receiving slot 631 are defined by a variety of surfaces and/or structure. For example, when the rotational connector 630 is top loaded upon the screw head 4, the bottom 634 of the middle portion 630*c* does not substantially extend downwardly past the upper extent of the primary fusion rod 2.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The foregoing description of several embodiments of the invention has been presented for purposes of illustration. It is not intended to be exhaustive or to limit the invention to the precise steps and/or forms disclosed, and obviously many modifications and variations are possible in light of the above teaching. It is intended that the scope of the invention and all equivalents be defined by the claims appended to the application once filed as a non-provisional application.

The invention claimed is:

1. A method of implanting a rotational connector, said rotational connector having a first end and a second end, said method comprising:
    opening a first surgical site in a patient to access a primary fusion site, said primary fusion site including a primary fusion rod having a longitudinal rod axis and a first end and a second end, and a pedicle screw engaged in a vertebra, wherein said first end of said primary fusion rod terminates at a first distance away from an outer surface of said pedicle screw measured in a first direction, said first direction generally parallel to said longitudinal rod axis;
    inserting said rotational connector in a first orientation through said first surgical site and onto said pedicle screw in a second direction, wherein said second direction is generally perpendicular to said first direction, and wherein said first orientation is disposed at an angle to said longitudinal rod axis;
    rotating said rotational connector from said first orientation to a second orientation, wherein in said second orientation said first end of said rotational connector matingly receives therewithin said second end of said primary fusion rod;
    inserting a set screw into said first end of said rotational connector to secure said rotational connector to said primary fusion rod;
    inserting a first end of a revision rod into said second end of said rotational connector;
    inserting a set screw into said second end of said rotational connector to secure said rotational connector to said revision rod.

2. The method of claim 1 wherein the step of rotating said rotational connector from said first orientation to said second orientation includes wherein in said second orientation said second end of said rotational connector matingly receives therewithin said first end of said primary fusion rod.

3. The method of claim 1 further comprising the step of positioning said revision rod at an angle relative to said second end of said rotational connector.

4. The method of claim 3 wherein the step of position said revision rod at said angle relative to said second end of said rotational connector includes spherical angulation.

5. The method of claim 1 wherein the step of rotating said rotational connector from said first orientation to said second orientation includes rotating said rotational connector about a screw head of said pedicle screw after said pedicle screw is inserted into said rotational connector.

6. The method of claim 1 further comprising the step of axial alignment of said revision rod and said primary fusion rod.

7. The method of claim 1 wherein the step of rotating said rotational connector from said first orientation to said second orientation includes rotating an acute angle between said first orientation and said second orientation.

8. The method of claim 1 wherein said acute angle is 30 degrees.

* * * * *